(12) United States Patent
Takamoto

(10) Patent No.: US 12,293,526 B2
(45) Date of Patent: May 6, 2025

(54) GAZE ESTIMATION SYSTEM, GAZE ESTIMATION METHOD, AND COMPUTER PROGRAM

(71) Applicant: NEC Corporation, Tokyo (JP)

(72) Inventor: Makoto Takamoto, Tokyo (JP)

(73) Assignee: NEC CORPORATION, Tokyo (JP)

( * ) Notice: Subject to any disclaimer, the term of this patent is extended or adjusted under 35 U.S.C. 154(b) by 351 days.

(21) Appl. No.: 17/796,708

(22) PCT Filed: Feb. 10, 2020

(86) PCT No.: PCT/JP2020/005118
§ 371 (c)(1),
(2) Date: Aug. 1, 2022

(87) PCT Pub. No.: WO2021/161380
PCT Pub. Date: Aug. 19, 2021

(65) Prior Publication Data
US 2023/0058491 A1 Feb. 23, 2023

(51) Int. Cl.
*G06T 7/20* (2017.01)
*G06T 7/70* (2017.01)
(Continued)

(52) U.S. Cl.
CPC .................. *G06T 7/20* (2013.01); *G06T 7/70* (2017.01); *G06V 40/40* (2022.01); *G06V 40/67* (2022.01);
(Continued)

(58) Field of Classification Search
CPC .. G06T 7/20; G06T 7/70; G06V 40/67; G06V 2201/07
See application file for complete search history.

(56) References Cited

U.S. PATENT DOCUMENTS

2007/0263908 A1 11/2007 Tsukahara
2015/0085251 A1* 3/2015 Larsen .................... G06F 3/013
351/206
(Continued)

FOREIGN PATENT DOCUMENTS

EP 2441383 B1 4/2012
EP 3236338 B1 10/2017
(Continued)

OTHER PUBLICATIONS

International Search Report for PCT Application No. PCT/JP2020/005118, mailed on Mar. 31, 2020.
(Continued)

*Primary Examiner* — Myron Wyche

(57) ABSTRACT

A gaze estimation system includes: a display control unit that allows a point to look at where a target person looks at to be displayed to move in a predetermined moving aspect; a detection unit that detects a movement of eyes of the target person from an image of the target person; and a tracking determination unit that determines whether or not the eyes of the target person are following the point to look at on the basis of a relationship between the eye movement and a movement of the point to look at. According to such a gaze estimation system, the eye movement of the target person can be detected more appropriately.

8 Claims, 14 Drawing Sheets

(51) Int. Cl.
*G06V 40/40* (2022.01)
*G06V 40/60* (2022.01)

(52) U.S. Cl.
CPC .............. *G06T 2207/30201* (2013.01); *G06T 2207/30241* (2013.01); *G06V 2201/07* (2022.01)

(56) References Cited

U.S. PATENT DOCUMENTS

| | | | | |
|---|---|---|---|---|
| 2016/0335483 | A1* | 11/2016 | Pfursich | G06V 40/174 |
| 2017/0243063 | A1 | 8/2017 | Kaneko et al. | |
| 2018/0008141 | A1* | 1/2018 | Krueger | A61B 5/7257 |
| 2021/0073364 | A1 | 3/2021 | Sakai | |
| 2021/0137378 | A1 | 5/2021 | Hayashi | |

FOREIGN PATENT DOCUMENTS

| | | |
|---|---|---|
| JP | 2003-038443 A | 2/2003 |
| JP | 2006-136450 A | 6/2006 |
| JP | 2012-216123 A | 11/2012 |
| JP | 2013-255781 A | 12/2013 |
| JP | 2014-068933 A | 4/2014 |
| JP | 2016-151849 A | 8/2016 |
| JP | 2017-107546 A | 6/2017 |
| JP | 2017-151556 A | 8/2017 |
| JP | 2017-189470 A | 10/2017 |
| JP | 2018-015218 A | 2/2018 |
| JP | 2018-108167 A | 7/2018 |
| JP | 2019-024608 A | 2/2019 |
| JP | 2020-018470 A | 2/2020 |
| WO | 2014/204904 A1 | 12/2014 |
| WO | 2015/164807 A1 | 10/2015 |
| WO | 2019/151368 A1 | 8/2019 |
| WO | 2020/026574 A1 | 2/2020 |

OTHER PUBLICATIONS

JP Office Action for Japanese Patent Application No. 2023-136501, mailed on Jun. 4, 2024 with English Translation.
Extended European Search Report for EP Application No. 20918302.9, dated on Mar. 2, 2023.

* cited by examiner

GAZE ESTIMATION SYSTEM, GAZE ESTIMATION METHOD, AND COMPUTER PROGRAM

This application is a National Stage Entry of PCT/JP2020/005118 filed on Feb. 10, 2020, the contents of all of which are incorporated herein by reference, in their entirety.

TECHNICAL FIELD

This disclosure relates to a gaze estimation system, a gaze estimation method, and a computer program that estimate a gaze or a line of sight of a target person.

BACKGROUND ART

This type of system is known to detect the gaze of a target person. For example, Patent Literature 1 discloses a technique/technology in which a visual stimulus information determined in advance is displayed on a display, and a point of gaze is estimated from the visual stimulus information and the movement of eyes of a subject. Patent Literature 2 discloses a technique/technology in which a detection process of detecting the gaze, such as corneal reflex, is performed by using each of images captured at a predetermined frame rate. Patent Literature 3 discloses a technique/technology in which a gaze detection process is performed by using a user's image received from an imaging apparatus.

CITATION LIST

Patent Literature

Patent Literature 1: JP2019-024608A
Patent Literature 2: JP2017-107546A
Patent Literature 3: JP2018-015218A

SUMMARY

Technical Problem

A method of having a target person look at a point to look at that is not moving, not only places a heavy burden on the target person, but also induces an unconscious wandering gaze. In each of the above-described Patent Literatures, a countermeasure for the wandering gaze is not sufficient and there is room for improvement.

It is an example object of this disclosure to provide a gaze estimation system, a gaze estimation method, and a computer program for solving the above-described problems.

Solution to Problem

A gaze estimation system according to an example aspect of this disclosure includes: a display control unit that allows a point to look at where a target person looks at to be displayed to move in a predetermined moving aspect; a detection unit that detects a movement of eyes of the target person from an image of the target person; and a tracking determination unit that determines whether or not the eyes of the target person are following the point to look at on the basis of a relationship between the eye movement and a movement of the point to look at.

A gaze estimation method according to an example aspect of this disclosure includes: allowing a point to look at where a target person looks at to be displayed to move in a predetermined moving aspect; detecting a movement of eyes of the target person from an image of the target person; and determining whether or not the eyes of the target person are following the point to look at on the basis of a relationship between the eye movement and a movement of the point to look at.

A computer program according to an example aspect of this disclosure operates a computer: to allow a point to look at where a target person looks at to be displayed to move in a predetermined moving aspect; to detect a movement of eyes of the target person from an image of the target person; and to determine whether or not the eyes of the target person are following the point to look at on the basis of a relationship between the eye movement and a movement of the point to look at.

DESCRIPTION OF EXAMPLE EMBODIMENTS

Hereinafter, a gaze estimation system, a gaze estimation method, and a computer program according to example embodiments will be described with reference to the drawings.

First Example Embodiment

A gaze estimation system according to a first example embodiment will be described with reference to FIG. 1 to FIG. 3.

(System Configuration)

First, with reference to FIG. 1, a description will be given to an overall configuration of the gaze estimation system according to the first example embodiment. FIG. 1 is a block diagram illustrating the overall configuration of the gaze estimation system according to the first example embodiment.

Figure 1:
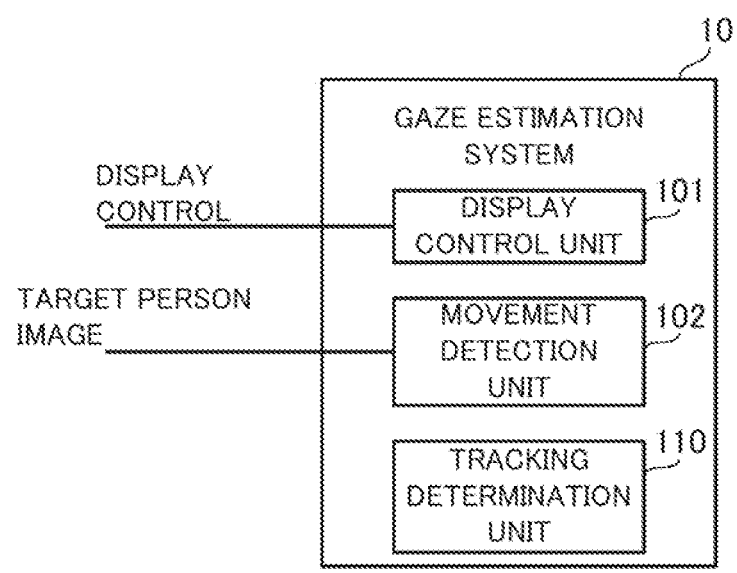
FIG. 1 is a block diagram illustrating an overall configuration of a gaze estimation system according to a first example embodiment.

As illustrated in FIG. 1, a gaze estimation system 10 according to the first example embodiment includes, as functional blocks for realizing its function, a display control unit 101, a movement detection unit 102, and a tracking determination unit 110.

The display control unit 101 is configured to allow a point to look at to be displayed, for example, on a display apparatus provided with a display or the like. The display control unit 101 performs a display control such that the point to look at moves along a predetermined movement path. More specifically, the display control unit 101 controls respective parameters related to a behavior and a display aspect of the point to look at, such as the movement path, movement velocity, size, color, or the like of the point to look at. Specific display examples of the point to look at will be described in detail later.

The movement detection unit 102 estimates a target person's eye movement from an image of the target person (i.e., a person who is looking at the point to look at). The movement detection unit 102 may obtain the image of the target person, for example, from a camera or the like installed around the display apparatus on which a gaze part is displayed. For example, the movement detection unit 102 may detect a face area of the target person from the image of the target person and may detect the eye movement from an image of the face area. Furthermore, the movement detection unit 102 may estimate a gaze or a line of sight of the target person (e.g., which position of a display unit 20 the target person is looking at) from the eye movement in the image of the target person. Incidentally, a detailed description of a more specific method of detecting the eye movement will be omitted here because it is possible to appropriately adopt the existing techniques/technologies.

The tracking determination unit 110 is configured to determine whether or not the eyes of the target person are following the point to look at on the basis of a relationship between the movement of the point to look at controlled by the display control unit 101 and the eye movement detected by the movement detection unit 102. For example, the tracking determination unit 110 may determine that the eyes of the target person are following the point to look at when the eyes of the target person are moving to follow the movement of the point to look at. There is, however, a certain amount of time delay between the movement of the point to look at and the movement of the target person (a deviation caused by a delayed response). Therefore, the tracking determination unit 110 may determine the tracking in consideration of such a time delay. Furthermore, when there is no deviation at all between the movement of the point to look at and the movement of the eyes of the target person, the tracking determination unit 110 may determine that the eyes of the target person are not following the point to look at (e.g., it may determine that some fraud is being performed).

(Hardware Configuration)

Figure 2:
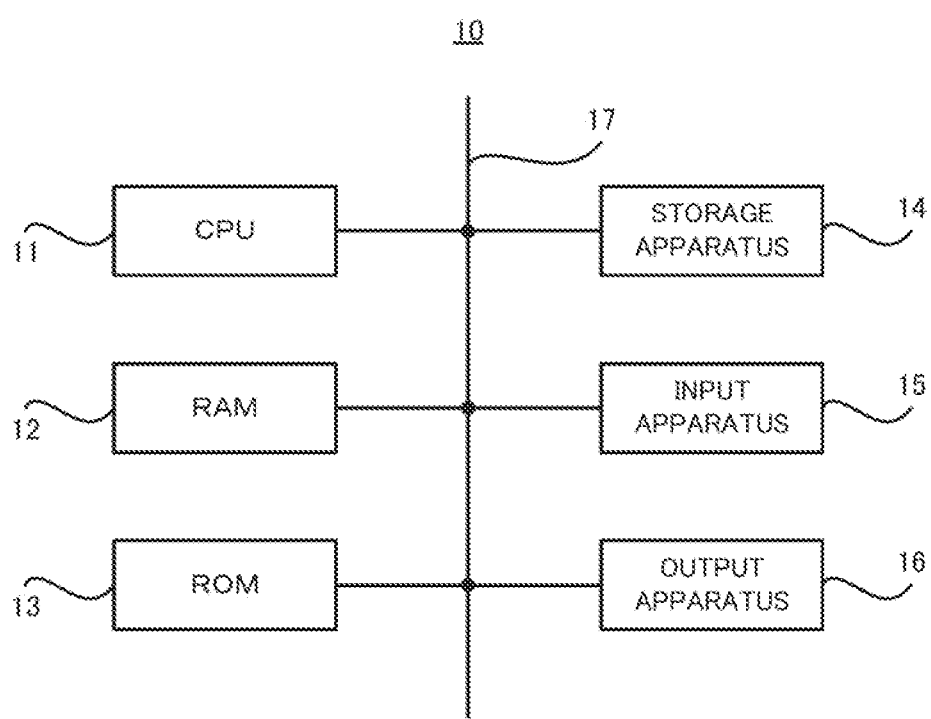
FIG. 2 is a block diagram illustrating a hardware configuration of the gaze estimation system according to the first example embodiment.

Next, with reference to FIG. 2, a hardware configuration of the gaze estimation system 10 according to the first example embodiment. FIG. 2 is a block diagram illustrating the hardware configuration of the gaze estimation system according to the first example embodiment.

As illustrated in FIG. 2, the gaze estimation system 10 according to the first example embodiment includes a CPU (Central Processing Unit) 11, a RAM (Random Access Memory) 12, a ROM (Read Only Memory) 13, and a storage apparatus 14. The gaze estimation system 10 may further include an input apparatus 15 and an output apparatus 16. The CPU 11, the RAM 12, the ROM 13, the storage apparatus 14, the input apparatus 15, and the output apparatus 16 are connected through a data bus 17. The gaze estimation system 10 may include a plurality of CPUs 11, RAMs 12, ROMs 13, storage apparatuses 14, input apparatuses 15, and output apparatuses 16.

The CPU 11 reads a computer program. For example, the CPU 11 is configured to read a computer program stored in at least one of the RAM 12, the ROM 13 and the storage apparatus 14. Alternatively, the CPU 11 may read a computer program stored by a computer readable recording medium by using a not-illustrated recording medium reading apparatus. The CPU 11 may obtain (i.e., read) a computer program from a not-illustrated apparatus that is located outside the gaze estimation system 10 through a network interface. The CPU 11 controls the RAM 12, the storage apparatus 14, the input apparatus 15, and the output apparatus 16 by executing the read computer program. Especially in the first example embodiment, when the computer program read by CPU 11 is executed, a functional block for controlling the display of the point to look at, estimating the eye movement of the target person, and determining the tracking is implemented in the CPU 11 (see FIG. 1).

The RAM 12 temporarily stores the computer program to be executed by the CPU 11. The RAM 12 temporarily stores the data that is temporarily used by the CPU 11 when the CPU 11 executes the computer program. The RAM 12 may be, for example, a D-RAM (Dynamic RAM).

The ROM 13 stores the computer program to be executed by the CPU 11. The ROM 13 may otherwise store fixed data. The ROM 13 may be, for example, a P-ROM (Programmable ROM).

The storage apparatus 14 stores the data that is stored for a long term by the gaze estimation system 10. The storage apparatus 14 may operate as a temporary storage apparatus of the CPU 11. The storage apparatus 14 may include, for example, at least one of a hard disk apparatus, a magneto-optical disk apparatus, an SSD (Solid State Drive), and a disk array apparatus.

The input apparatus 15 is an apparatus that receives an input instruction from a user of the gaze estimation system 10. The input apparatus 15 may include, for example, at least one of a keyboard, a mouse, and a touch panel.

The output apparatus 16 is an apparatus that outputs information about the gaze estimation system 10 to the outside. For example, the output apparatus 16 may be a display apparatus (e.g., a display) that is configured to display the information about the gaze estimation system 10.

(Flow of Operation)

Next, with reference to FIG. 3, a description will be given to a flow of operation of the gaze estimation system 10 according to the first example embodiment. FIG. 3 is a flowchart illustrating the flow of the operation of the gaze estimation system according to the first example embodiment.

Figure 3:
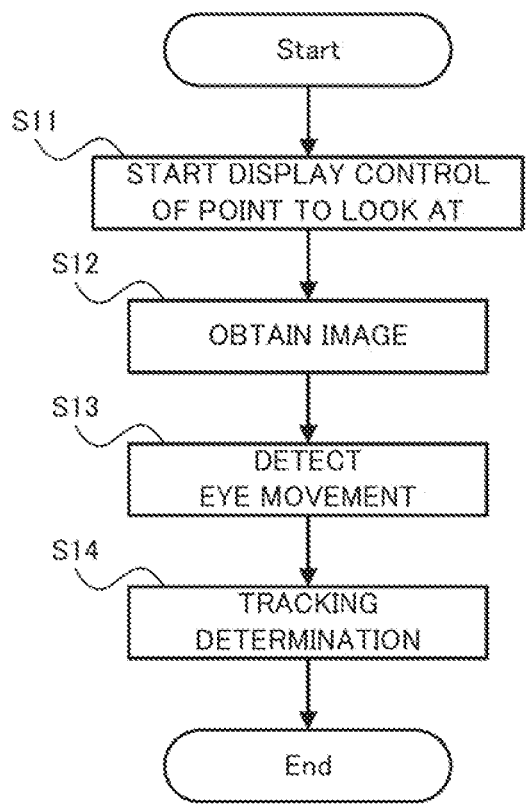
FIG. 3 is a flowchart illustrating a flow of operation of the gaze estimation system according to the first example embodiment.

As illustrated in FIG. 3, in operation of the gaze estimation system 10 according to the first example embodiment, first, the display control unit 101 starts the display control of the point to look at (step S11). The display control of the point to look at may be started, for example, by the target person's terminal operation, or may be automatically started by detecting the presence of the target person around a display apparatus or the like on which the point to look at is displayed.

When the display control of the point to look at is started, the movement detection unit 102 obtains the image of the target person (step S12). Then, the movement detection unit 102 detects the eye movement of the target person from the obtained image of the target person (step S13).

Subsequently, the tracking determination unit 110 determines whether or not the eyes of the target person are following the point to look at on the basis of the relationship between the movement of the point to look at controlled by the display control unit 101 and the eye movement detected by the movement detection unit 102 (step S14).

(Technical Effect)

Next, an example of a technical effect obtained by the gaze estimation system 10 according to the first example embodiment will be described.

As described in FIG. 1 to FIG. 3, according to the gaze estimation system 10 in the first example embodiment, it is possible to detect the eye movement of the target person by having the target person look at the point to look at. Here, in particular, since the point to look at is controlled to move, it is possible to suppress a wandering gaze of the target person, for example, as compared with a case of having the target person look at a point to look at that is not moving.

Furthermore, in the first example embodiment, whether or not the target person is following the point to look at is determined from the detected eye movement. It is thus possible to determine whether or not the target person is normally looking at the point to look at that is moving. A determination result can be used not only to determine whether or not the eye movement can be appropriately detected, but also, for example, to correct a point of gaze of the target person or to detect spoofing, as in second and third example embodiments described later.

Second Example Embodiment

A gaze estimation system according to a second example embodiment will be described with reference to FIG. 4 to FIG. 10. The second example embodiment is partially different from the first example embodiment described above only in operation (mainly, an operation related to the display of the point to look at), and is generally the same in the other parts. Therefore, the parts that differ from the first example embodiment will be described in detail below, and the other overlapping parts will not be described as appropriate.

(System Configuration)

Since a configuration of the gaze estimation system according to the second example embodiment may be the same as that of the gaze estimation system according to the first example embodiment (see FIG. 1), a description thereof will be omitted. Furthermore, since a hardware configuration of the gaze estimation system according to the second example embodiment may be the same as that of the gaze position estimation system 10 according to the first example embodiment (see FIG. 2), a description thereof will be omitted.

(Flow of Operation)

Since a flow of the operation of the gaze estimation system 10 according to the second example embodiment may be the same as that of the gaze estimation system 10 according to the first example embodiment (see FIG. 3), a description thereof will be omitted. In the gaze estimation system 10 according to the second example embodiment, however, the display control unit 101 controls a display aspect of the point to look at or a display aspect of a trajectory of the point to look at as follows.

(Display Aspect of Point to Look at)

Figure 4:
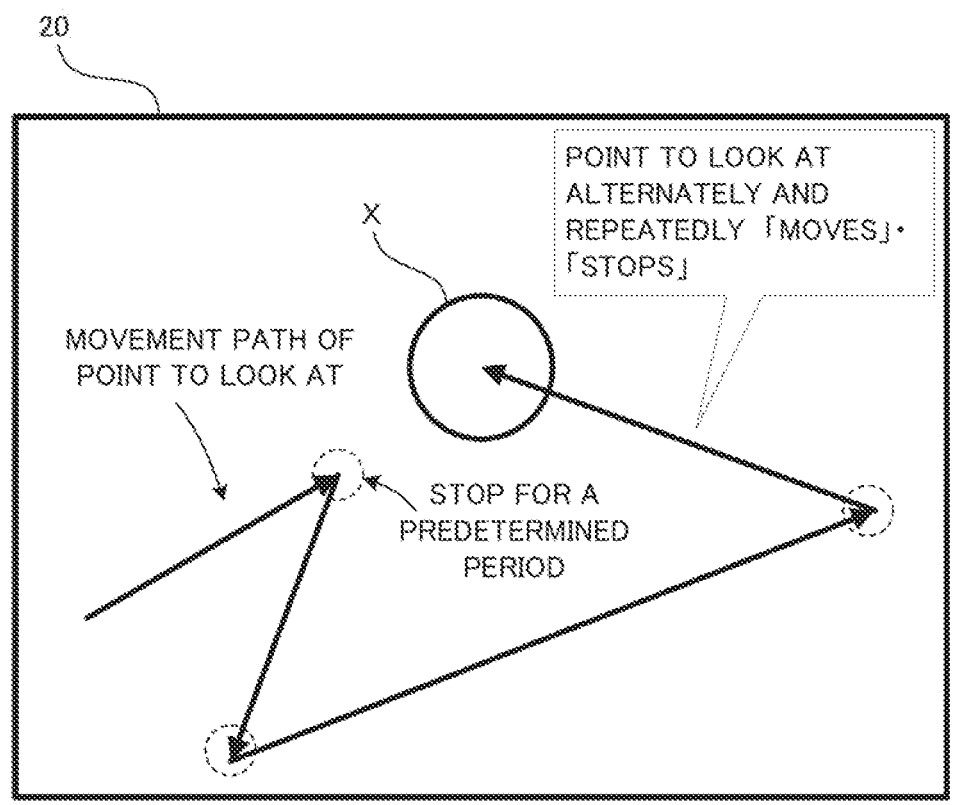
FIG. 4 is version 1 of a conceptual diagram illustrating a display aspect of a point to look at by a gaze estimation system according to a second example embodiment.
Figure 5:
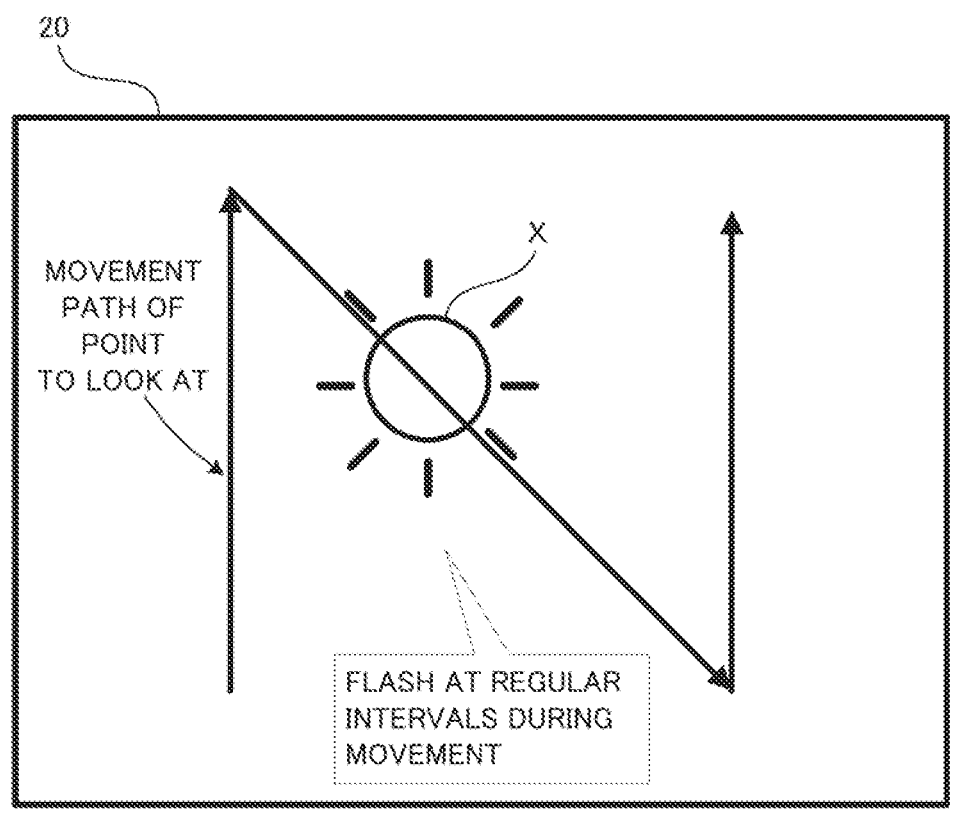
FIG. 5 is version 2 of a conceptual diagram illustrating a display aspect of the point to look at by the gaze estimation system according to the second example embodiment.
Figure 6:
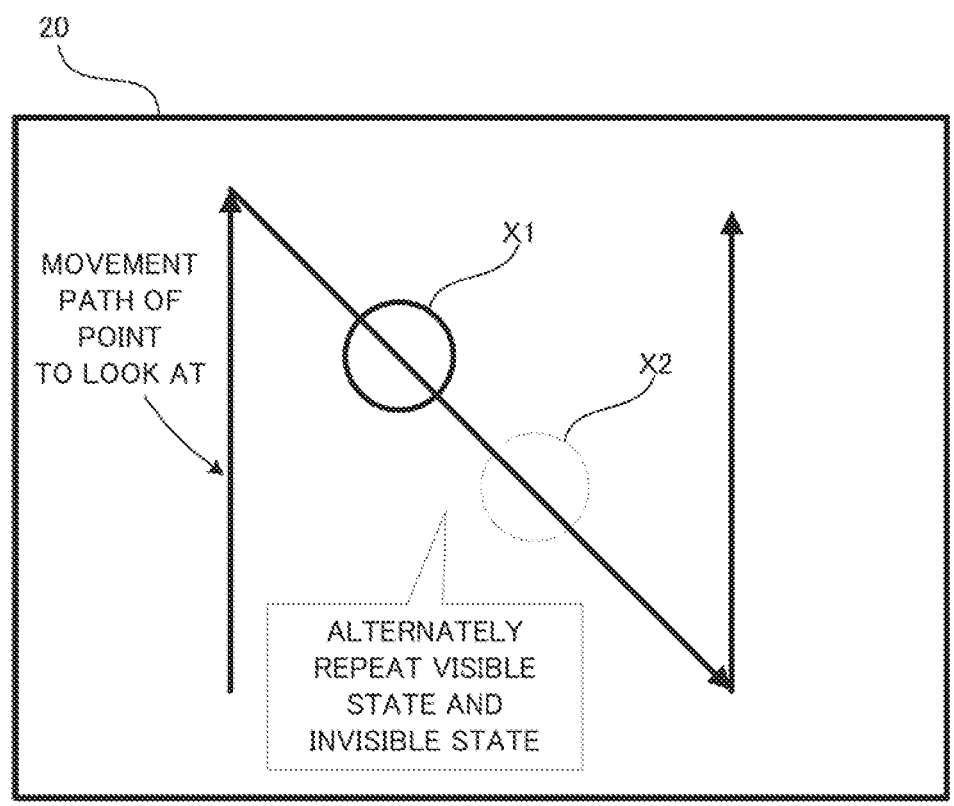
FIG. 6 is version 3 of a conceptual diagram illustrating a display aspect of the point to look at by the gaze estimation system according to the second example embodiment.
Figure 7:
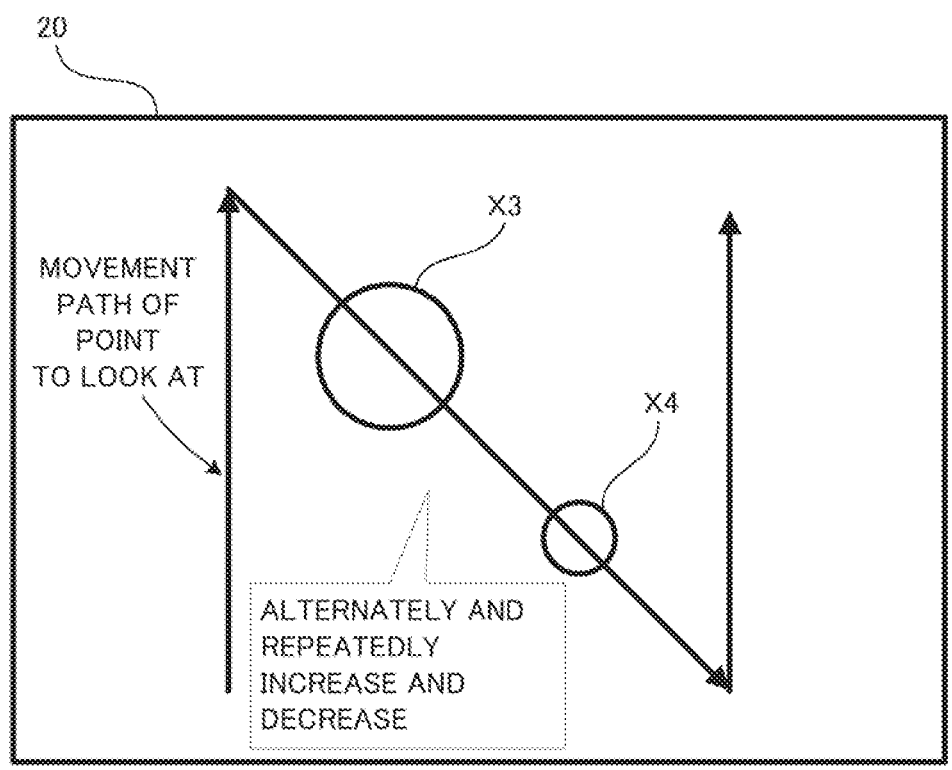
FIG. 7 is version 4 of a conceptual diagram illustrating a display aspect of the point to look at by the gaze estimation system according to the second example embodiment.

The display aspect of the point to look at in the gaze estimation system 10 according to the second example embodiment will be described with reference to FIG. 4 to FIG. 7. FIG. 4 is version 1 of a conceptual diagram illustrating the display aspect of the point to look at by the gaze estimation system according to the second example embodiment. FIG. 5 is version 2 of a conceptual diagram illustrating a display aspect of the point to look at by the gaze estimation system according to the second example embodiment. FIG. 6 is version 3 of a conceptual diagram illustrating a display aspect of the point to look at by the gaze estimation system according to the second example embodiment. FIG. 7 is version 4 of a conceptual diagram illustrating a display aspect of the point to look at by the gaze estimation system according to the second example embodiment.

As illustrated in FIG. 4, a point X to look at moves on a display surface of a display unit 20 so as to alternately and repeatedly move and stop along a predetermined trajectory. More specifically, the point X to look at repeats the following; it moves on a predetermined straight line and stops at an end point of the line for a predetermined period (e.g., a few seconds), and moves therefrom again on another straight line and stops at an end point of the straight line for a predetermined period. In this way, it is possible to easily have the target person look at the point X to look at. The point X to look at preferably moves to pass through all points on the display surface of the display unit 20. Here, a shape of the point X to look at is, for example, an ellipse, and a position of the point X to look at is, for example, a center position of the point X to look at. The shape and position of the point X to look at is not limited thereto.

The target person is asked to follow such a movement of the point X to look at with the eyes. To have the target person follow the point X to look at, a specific instruction may be outputted to the target person before starting the display control of the point X to look at. For example, an instruction may be displayed by a sentence or the like so as to follow the point X to look at on the display unit 20. Alternatively, the display control may be performed such that the target person naturally follows the point X to look at with the eyes. For example, the point X to look at may be displayed as a character or object that attracts the target person's interest.

Incidentally, the movement velocity and size of the point X to look at are set in advance. However, depending on a reaction of the target person, the movement velocity of the point X to look at may be changed as appropriate. For example, for a target person whose gaze movement with respect to the movement of the point to look at delays relatively significantly, the movement of the point X to look at may be made slower. Alternatively, the size of the point X to look at may be appropriately changed depending on the reaction of the target person. For example, for a target person with relatively large variation in point of gaze, the size of the point X to look at may be increased. In addition, depending on the reaction of the target person, both of the movement velocity and the size of the point X to look at may be changed as appropriate. The control of changing the movement velocity of the point X to look at or the control of changing the size of the point X to look at may be performed by using a result obtained immediately after the display control of the point X to look at is started (e.g., a result measured when the point to look at moves on the first straight line).

As illustrated in FIG. 5, the point X to look at may be controlled to flash (in other words, may be highlighted) at predetermined intervals during the movement. In this way, it is possible to easily have the target person look at the point X to look at. In addition, as the point X to look at flashes at regular intervals, the target person easily predicts the movement of the point X to look at. This makes it easy to reduce a time delay in a parallax (i.e., a delay of a gaze movement with respect to the movement of the point to look at) to a constant value. Even in the display aspect illustrated in FIG. 5, as described in FIG. 4, the point X to look at may be alternately moved and stopped.

As illustrated in FIG. 6, the point X to look at may be controlled to alternately repeat a visible state (X1 in the figure) and an invisible state (X2 in the figure) during the movement. Even in such a case, the target person can easily look at the point X to look at. In addition, as the point X to look at periodically repeats the visible state and the invisible state, the target person easily predicts the movement of the point X to look at. Therefore, it becomes easy to reduce the time delay in the parallax to a constant value. Even in the display aspect illustrated in FIG. 6, the point X to look at may move and stop, alternately and repeatedly, as described in FIG. 4.

As illustrated in FIG. 7, the point X to look at may be controlled to alternately repeat a state of being displayed large (X3 in the figure) and a state of being displayed small (X4 in the figure) during the movement. Even in such a case, the target person can easily look at the point X to look at. In addition, as the size of the point X to look at changes periodically, the target person easily predicts the movement of the point X to look at. Therefore, it becomes easy to reduce the time delay in the parallax to a constant value. Even in the display aspect illustrated in FIG. 7, the point X to look at may move and stop, alternately and repeatedly, as described in FIG. 4.

Furthermore, in addition to the point X to look at, a numeral for counting may be displayed. The numeral, for example, may be counted up from an initial value set in advance to an upper limit, or may be counted down from the initial value set in advance to a lower limit. The numeral may be counted by the lapse of time (e.g., every second). Furthermore, it may be counted in a period from the point X to look at starts to move until it stops, may be counted every time it flashes, or may be counted when the position of the point X to look at and the position of the eyes are continuously within a predetermined distance.

(Technical Effect of Display Aspect of Point to Look at)

Next, an example of a technical effect obtained by the gaze estimation system 10 according to the display aspect of the point to look at in the second example embodiment will be described.

According to the gaze estimation system 10 in the second example embodiment, the display aspect of the point to look at is controlled as illustrated in FIG. 4 to FIG. 7. Therefore, it becomes easier to have the target person look at the point X to look at. Each display aspect illustrated in FIG. 4 to FIG. 7 may be combined as appropriate. For example, the point X to look at that moves so as to alternately and repeatedly move and stop along a predetermined trajectory as in FIG. 4, may be controlled to flash at predetermined intervals during the movement as in FIG. 5.

(Display Aspect of Trajectory of Point to Look at)

Figure 8:
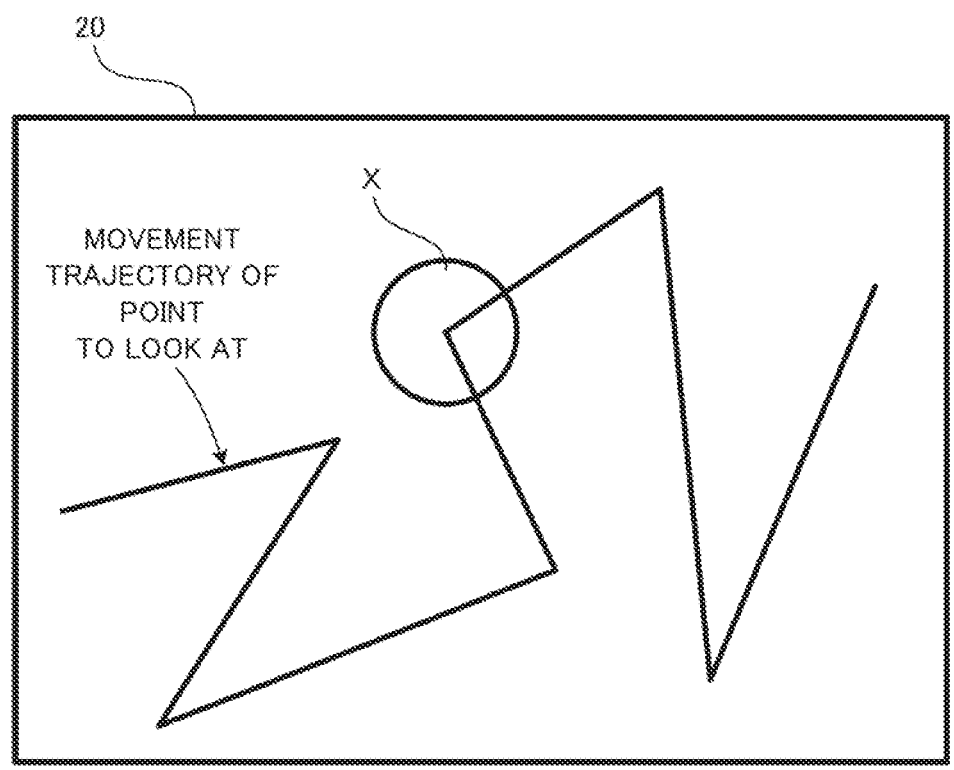
FIG. 8 is version 1 of a conceptual diagram illustrating a display aspect of a trajectory of the point to look at by the gaze estimation system according to a second example embodiment.
Figure 9:
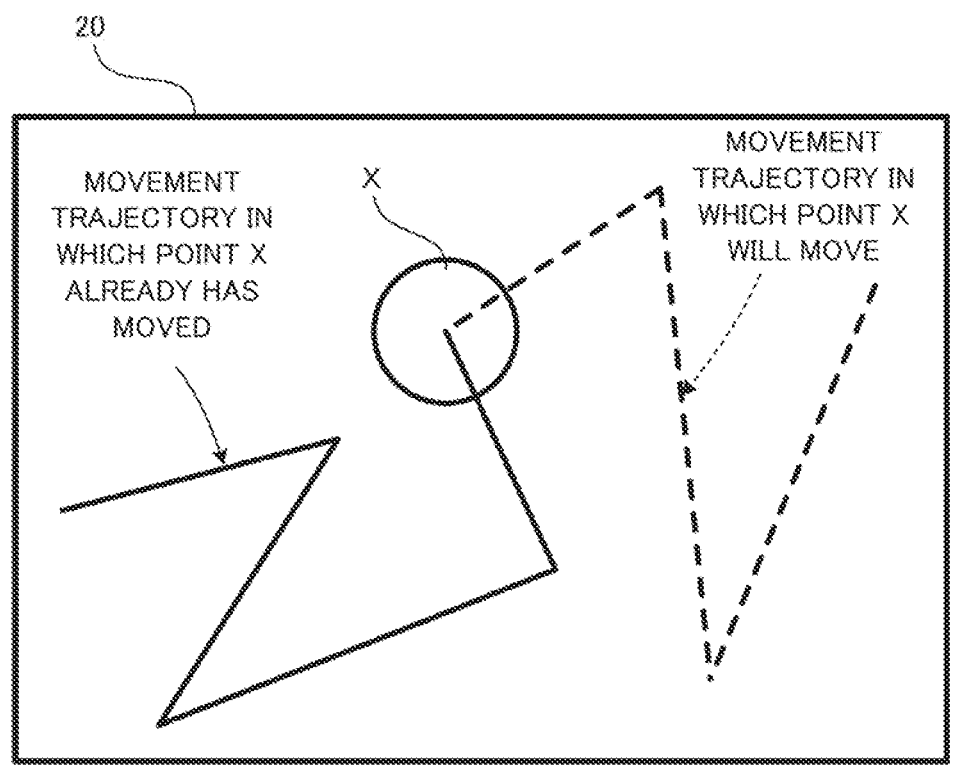
FIG. 9 is version 2 of a conceptual diagram illustrating a display aspect of the trajectory of the point to look at by the gaze estimation system according to a second example embodiment.
Figure 10:
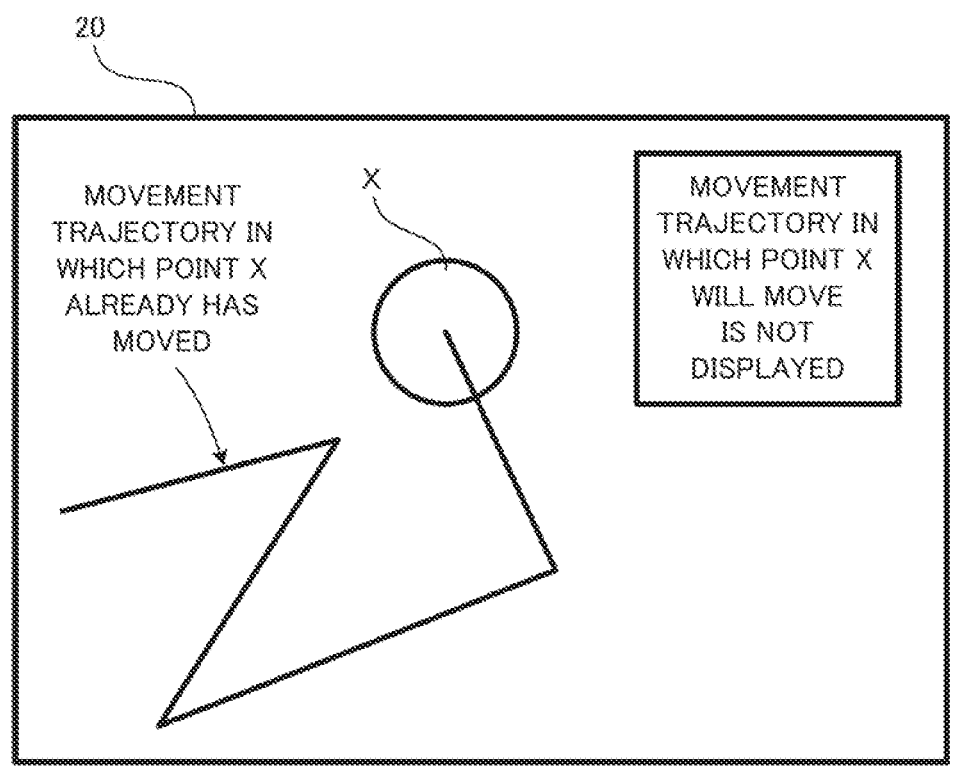
FIG. 10 is version 3 of a conceptual diagram illustrating a display aspect of the trajectory of the point to look at by the gaze estimation system according to a second example embodiment.

Next, the display aspect of the trajectory of the point X to look at will be described with reference to FIG. 8 to FIG. 10. FIG. 8 is version 1 conceptual diagram illustrating the display aspect of the trajectory of the point to look at by the gaze estimation system according to a second example embodiment. FIG. 9 is version 2 of a conceptual diagram illustrating a display aspect of the trajectory of the point to look at by the gaze estimation system according to a second example embodiment. FIG. 10 is version 3 of a conceptual diagram illustrating a display aspect of the trajectory of the point to look at by the gaze estimation system according to a second example embodiment.

As illustrated in FIG. 8, the movement trajectory of the point X to look at may be displayed. In this way, the target person can know how the point X to look at has moved so far, or how the point X to look at will move from now. This makes it easier for the target person to predict the movement of the point X to look at.

As illustrated in FIG. 9 and FIG. 10, the movement trajectory of the point X to look at may have different display aspects between a movement trajectory in which the point X has already moved and a movement trajectory in which the point X will move from now. Specifically, as illustrated in FIG. 9, while the movement trajectory in which the point X has already moved is displayed by a solid line, the movement trajectory in which the point X will move from now may be displayed by a dotted line. Alternatively, as illustrated in FIG. 10, while the movement trajectory in which the point X has already moved is displayed as normal, the movement trajectory in which the point X will move from now may not be displayed (i.e., only the movement trajectory in which the point X has already moved may be displayed).

(Technical Effect of Display Aspect of Trajectory of Point to Look at)

Next, an example of a technical effect obtained by the gaze estimation system 10 according to the display aspect of the trajectory of the point to look at in the second example embodiment will be described.

According to the gaze estimation system 10 in the second example embodiment, the display aspect of the trajectory of the point to look at is controlled as illustrated in FIG. 8 to FIG. 10. Therefore, it becomes easy for the target person to predict the movement of the point X to look at, which makes it easy to reduce the time delay in the parallax to a constant value. An example of a technical effect obtained by reducing the time delay in the parallax to a constant value will be described in detail in a third example embodiment described later.

Third Example Embodiment

A gaze estimation system according to a third example embodiment will be described with reference to FIG. 11 and FIG. 12. The third example embodiment exemplifies that the gaze estimation system functions as a system for correcting (calibrating) a point of gaze. The third example embodiment is partially different from the first and second example embodiments described above only in configuration and operation, and is generally the same in the other parts. Therefore, the parts that differ from the first and second example embodiments will be described in detail below, and the other overlapping parts will not be described as appropriate.

(System Configuration)

First, with reference to FIG. 11, a description will be given to an overall configuration of the gaze estimation system according to the third example embodiment. FIG. 11 is a block diagram illustrating the overall configuration of the gaze estimation system according to the third example embodiment. Since a hardware configuration of the gaze estimation system according to the third example embodiment may be the same as that of the gaze position estimation system 10 according to the first example embodiment (see FIG. 2), a description thereof will be omitted.

Figure 11:
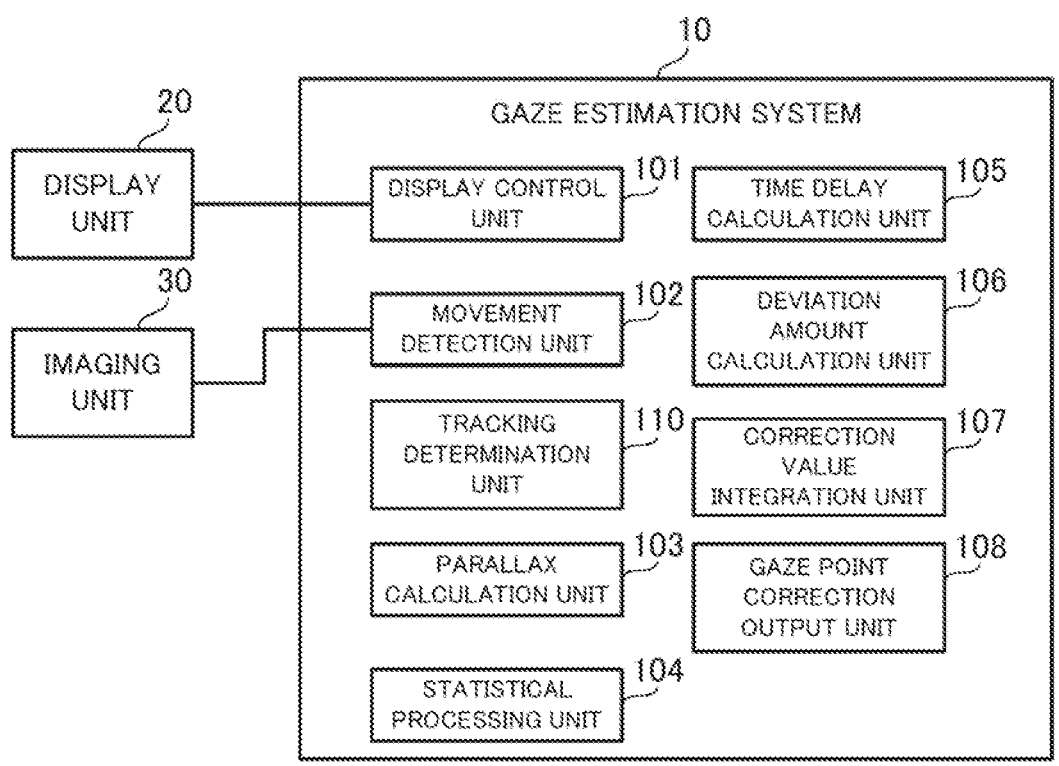
FIG. 11 is a block diagram illustrating an overall configuration of a gaze estimation system according to a third example embodiment.

As illustrated in FIG. 11, the gaze estimation system 10 according to the third example embodiment is connected to the display unit 20 and an imaging unit 30. The display unit 20 is a display located where the target person, who is a target for estimating a point of gaze, can visually recognize it, and displays a point to look at for estimating the point of gaze. The display control of the point to look at on the display unit 20 is performed by the gaze estimation system 10. The imaging unit 30 is a camera installed around the display unit 20, and is located where an image of the target person (in particular, an image of a face periphery) can be captured. The image of the target person captured by the imaging unit 30 is configured to be outputted to the gaze estimation system 10.

The gaze estimation system 10 according to the third example embodiment includes, in addition to the components of the first example embodiment (see FIG. 1), a parallax calculation unit 103, a statistical processing unit 104, a time delay calculation unit 105, a deviation amount calculation unit 106, a correction value integration unit 107, and a gaze point correction output unit 108.

The parallax calculation unit 103 calculates a parallax that is a difference between the position of the point to look at controlled by the display control unit 101 and the point of gaze of the target person estimated by the movement detection unit 102. The parallax calculated by the parallax calculation unit 103 is calculated as a value including a random statistical error or a time delay. The parallax calculation unit 103 may be implemented as a functional block having the function described above, for example, in the CPU 11 (see FIG. 1).

The statistical processing unit 104 is configured to perform a statistical process for removing the statistical error included in the parallax calculated by the parallax calculation unit 103. Specifically, the statistical processing unit 104 removes the statistical error by time-averaging the parallax calculated by the parallax calculation unit 103, for a certain period of time. Note that the above-described statistical process is merely an example, and the statistical error may be removed by using another statistical process. The statistical processing unit 104 may be implemented as a functional block having the function described above, for example, in the CPU 11 (see FIG. 1).

The time delay calculation unit 105 is configured to calculate the time delay included in the parallax calculated by the parallax calculation unit 103. The time delay calculation unit 105 calculates the time delay in the parallax, at least on the basis of the parallax when the point to look at is moving. The time delay calculation unit 105 may be implemented as a functional block having the function described above, for example, in the CPU 11 (see FIG. 1).

The deviation amount calculation unit 106 calculates a deviation amount between the point of gaze estimated by the movement detection unit 102 and a true value of the point of gaze (i.e., an actual position where the target person is looking at), on the basis of the parallax from which the statistical error is removed by the statistical processing unit 104 and the time delay calculated by the time delay calculation unit 105. The deviation amount calculation unit 106 may be implemented as a functional block having the function described above, for example, in the CPU 11 (see FIG. 1).

The correction value integration unit 107 calculates a correction value for the point of gaze estimated by the movement detection unit 102 (in other words, a correction amount for reducing the deviation of the point of gaze), on the basis of the deviation amount calculated by the deviation amount calculation unit 106. Furthermore, the correction value integration unit 107 performs an integrated process on correction values calculated at a plurality of locations in the display unit 20, and generates a correction formula for correcting the point of gaze. By using this correction formula, it is possible to correct the point of gaze even for a point where the correction value is not actually calculated. The correction value integration unit 107 may be implemented as a functional block having the function described above, for example, in the CPU 11 (see FIG. 1).

The gaze point correction output unit 108 outputs the correction formula generated by the correction value integration unit 107, as information for calibrating the point of gaze. Incidentally, the gaze point correction output unit 108 may store the generated correction formula, and may have a function of correcting and outputting the point of gaze (i.e., a function of outputting a corrected point of gaze). The gaze point correction output unit 108 may be implemented as a functional block having the function described above, for example, in the CPU 11 (see FIG. 1).

(Flow of Operation)

Next, with reference to FIG. 12, a flow of operation of the gaze estimation system 10 according to the third example embodiment will be described. FIG. 12 is a flowchart illustrating the flow of the operation of the gaze estimation system according to the third example embodiment.

Figure 12:
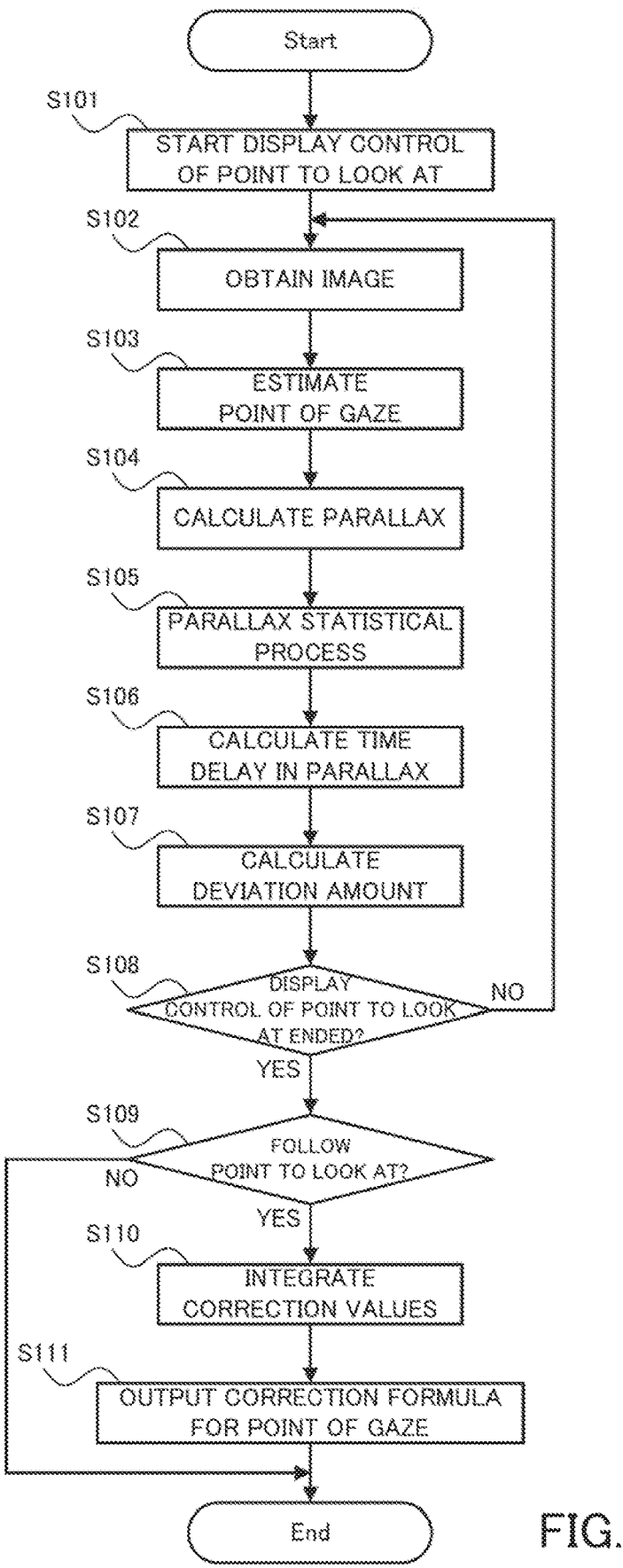
FIG. 12 is a flowchart illustrating a flow of operation of the gaze estimation system according to the third example embodiment.

As illustrated in FIG. 12, in operation of the gaze estimation system 10 according to the third example embodiment, first, the display control unit 101 starts the display control of the point to look at on the display unit 20 (step S101). The display control of the point to look at may be started, for example, by the target person's terminal operation, or may be automatically started by detecting the presence of the target person around the display unit 20.

When the display control of the point to look at is started, the movement detection unit 102 obtains the image of the target person from the imaging unit 30 (step S102). Then, the movement detection unit 102 estimates the point of gaze of the target person from the obtained image of the target person (step S103).

Subsequently, the parallax calculation unit 103 calculates the parallax that is a difference between the position of the point to look at and the estimated point of gaze (step S104). When the parallax is calculated, the statistical processing unit 104 performs the statistical process and removes the statistical error included in the parallax (step S105).

Thereafter, the time delay calculation unit 105 calculates the time delay that is occurring in the parallax (step S106). Then, the deviation amount calculation unit 106 calculates the deviation amount between the estimated point of gaze and the actual point of gaze, on the basis of the parallax from which the statistical error is removed and the time difference in the parallax (step S107).

When the deviation amount is calculated, it is determined whether or not the display control of the point to look at by the display control unit 101 is ended (step S108). That is, it is determined whether or not the point to look at repeatedly moves and stops along a predetermined path and completes the movement to an end point. When it is determined that the display control is not ended (the step S108: NO), the processing is repeated from the step S102 again. Thus, the deviation amount is calculated at several points along the movement path of the point to look at.

When it is determined that the display control is ended (the step S108: YES), the tracking determination unit 110 determines whether or not the eyes of the target person have followed the point to look at (step S109). Incidentally, the tracking determination unit 110 may determine whether or not the eyes of the target person are following the point to look at, before the display control is ended (i.e., while the point to look at is displayed). For example, the tracking determination unit 110 may determine whether or not the eyes of the target person are following the point to look at, at each time when the point X to look at stops. When it is determined that the eyes of the target person have not followed the point to look at (the step S109: NO), the subsequent processing is omitted and a series of operation steps is ended. It is because it is hardly possible to appropriately correct the point of gaze when the eyes of the target person are not following the point to look at.

On the other hand, when it is determined that the eyes of the target person have followed the point to look at (the step S109: YES), the correction value integration unit 107 calculates a plurality of correction values from the respective deviation amounts calculated at a plurality of locations, and performs the integrated process for the plurality of correction values (step S110). That is, the correction formula of the point of gaze is calculated on the basis of the plurality of correction values. Then, the gaze point correction output unit 108 outputs the correction formula generated by the correction value integration unit 107, as the information for calibrating the point of gaze (step S111).

(Correction of Point of Gaze)

Next, the correction of the point of gaze by the gaze estimation system 10 according to the second example embodiment will be specifically described. In the following, it is assumed that the point X to look at is displayed in the display aspect as illustrated in FIG. 6 described in the second example embodiment.

When the point of gaze estimated by the movement detection unit 102 of the gaze estimation system 10 according to the example embodiment is "Xgaze,est", the correction value is "ΔXcalib", and the statistical error is "ε", a true value of the point of gaze of the target person "Xgaze,true" can be expressed by the following equation (1).

$$\overrightarrow{X\text{gaze,true}} = \overrightarrow{X\text{gase,est}} + \overrightarrow{\Delta X\text{calib}} + \overrightarrow{\varepsilon} \quad (1)$$

When the parallax does not include the statistical error, the above equation (1) can also be expressed as illustrated in the following equation (2).

$$\overrightarrow{X\text{gaze,true}} = \overrightarrow{X\text{gase,est}} + \overrightarrow{\Delta X\text{calib}} \quad (2)$$

In this case, it is possible to make a calculation by ignoring "ε" in the following description.

Furthermore, when the position of the point X to look at is "Xc" and the time delay is "δXdelay", it can also be expressed as illustrated in the following equation (3).

$$\overrightarrow{X\text{gaze,true}} = \overrightarrow{Xc} + \overrightarrow{\delta X\text{delay}} \quad (3)$$

Furthermore, from the above equations (1) and (3), a parallax "Xgaze,est−Xc" calculated by the parallax calculation unit 103 can be expressed by the following equations (4).

$$\overrightarrow{X\text{gaze,est}} - \overrightarrow{Xc} = -\overrightarrow{\Delta X\text{calib}} - \overrightarrow{\varepsilon} + \overrightarrow{\delta X\text{delay}} \quad (4)$$

Here, the statistical error c can be removed by the statistical process performed by the statistical processing section 104. As a result, it is possible to calculate the correction value ΔXcalib by using Xgaze,est−Xc calculated by the parallax calculation unit 103 and a time delay δXdelay calculated by the time delay calculation unit 105.

The correction value ΔXcalib is calculated by using the parallax in a state where at least the point X to look at is moving. In the state where the point X to look at is moving, the time delay δXdelay is reduced when a sufficient time has elapsed after the point X to look at starts to move. Specifically, as the point to look at moves at a constant velocity, the target person can predict the movement of the point to look at, so that the time delay becomes small and approaches a constant value as much as possible. It is possible to estimate the time delay at this time, for example, from the point of gaze when the point X to look at is stopped, an elapsed time until the point of gaze is determined at the stopped position, or the like. Therefore, it is possible to calculate the correction value ΔXcalib, more easily and accurately, by using the parallax in the state where the point X to look at is moving. The parallax in the state where the point to look at is moving may be calculated, for example, at a middle point on a straight line on which the point X to look at moves.

The correction value ΔXcalib is calculated at a plurality of locations of the display unit 20. Then, the correction value integration unit 107 integrates the correction values ΔXcalib calculated at the plurality of locations to generate the correction formula of the point of gaze. The correction formula is generated as an equation such as the following equation (5), for example, including predetermined coefficients A and b.

$$\overrightarrow{X\text{gaze,true}} = A\overrightarrow{X\text{gase,est}} + \overrightarrow{b} \quad (5)$$

The correction value ΔXcalib may be calculated by integrating not only the correction value calculated in the state where the point X to look at is moving, but also the correction value calculated in a state where the point X to look at is stopped.

Furthermore, as the position Xc of the point X to look at, a position on the circumference of the point X to look at that is the closest to the point of gaze Xgaze,est (i.e., an intersection between a line segment connecting the point of gaze Xgaze,est and the center position of the point X to look at, and the circumference of the point X to look at) may be adopted.

In the above-described example, the parallax calculation, the parallax statistic process, the parallax time delay calculation, and the deviation amount calculation (i.e., the step S104 to the step S107 in FIG. 5) are sequentially performed; however, all of those may not be performed.

For example, the point of gaze may be corrected by performing the parallax calculation. In this way, it is possible to make a correction of reducing an influence of the parallax.

Alternatively, the point of gaze may be corrected by performing the parallax statistical process. In this way, it is possible to make a correction of reducing an influence by the statistical error of the parallax.

Alternatively, the point of gaze may be corrected by performing the parallax time delay calculation. In this way, it is possible to make a correction of reducing an influence by the time delay in the parallax.

Alternatively, the point of gaze may be corrected by performing the deviation amount calculation. In this way, it is possible to make a correction of reducing an influence by the deviation amount of the point of gaze.

Furthermore, at least two of the parallax calculation, the parallax statistic process, the parallax time delay calculation, and the deviation amount calculation may be combined and performed.

(Technical Effect)

Next, an example of a technical effect obtained by the gaze estimation system 10 according to the third example embodiment will be described.

As described in FIG. 11 and FIG. 12, according to the gaze estimation system 10 in the third example embodiment, it is possible to calculate the correction value for correcting the estimated point of gaze (in other words, the value for calibration) by having the target person to look at the point X to look at. Especially in the third example embodiment, as the correction value is calculated by using the parallax in the state where the point X to look at is moving, it is possible to reduce the influence of the time delay δXdelay, and to obtain the correction value even in a wider range than that in the case where the point X to look at is stationary. This makes it possible to accurately estimate where the target person is actually looking at.

Fourth Example Embodiment

Next, the gaze estimation system 10 according to a fourth example embodiment will be described with reference to FIG. 13 and FIG. 14. The fourth example embodiment exemplifies that the gaze estimation system 10 functions as a system for determining the spoofing of the target person will be described. The fourth example embodiment is partially different from the first to third example embodiments described above only in configuration and operation, and is generally the same in the other parts. Therefore, the parts that differ from the first to third example embodiments will be described in detail below, and the other overlapping parts will not be described as appropriate.

(System Configuration)

First, with reference to FIG. 13, a description will be given to an overall configuration of the gaze estimation system 10 according to the fourth example embodiment. FIG. 13 is a block diagram illustrating the overall configuration of the gaze estimation system according to the fourth example embodiment.

Since a hardware configuration of the gaze estimation system according to the fourth example embodiment may be the same as that of the gaze position estimation system 10 according to the first example embodiment (see FIG. 2), a description thereof will be omitted.

Figure 13:
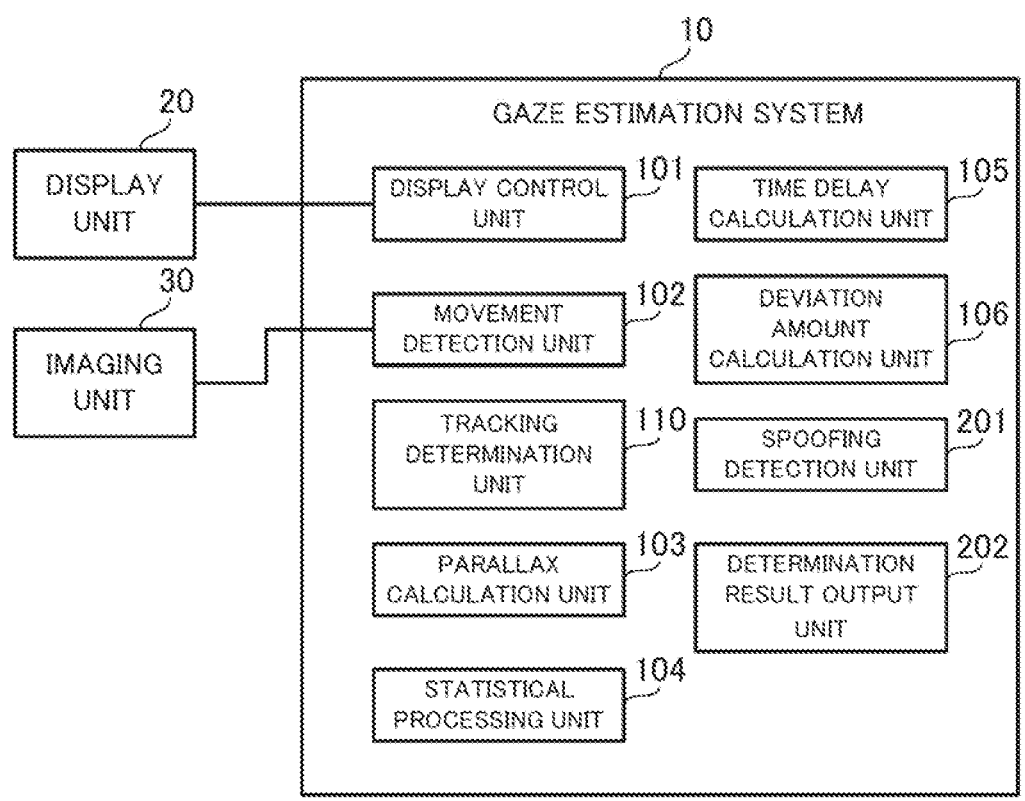
FIG. 13 is a block diagram illustrating an overall configuration of a gaze estimation system according to a fourth example embodiment.

As illustrated in FIG. 13, the gaze estimation system 10 according to the fourth example embodiment includes a spoofing detection unit 201 and a determination result output unit 202 in addition to the components of the gaze estimation system 10 according to the third example embodiment (see FIG. 1). More precisely, the gaze estimation system 10 according to the fourth example embodiment includes the spoofing detection unit 201 and the determination result output unit 202 in place of the correction value integration unit 107 and the gaze point correction output unit 108 according to the third example embodiment.

The spoofing detection unit 201 is configured to be detect that spoofing (i.e., an illegal operation using a video or the like) is performed on the basis of a determination result of the tracking determination unit 110. For example, if the target person is actually present in front of the imaging unit 30, the deviation amount is calculated as a value having an appropriate magnitude due to the time delay. On the other hand, when the target person is not actually present in front of the imaging unit 30 and a video or the like capturing the target person is directed to the imaging unit 30, the time delay characteristic of humans does not occur, the deviation amount is calculated as an extremely small value. Thus, the tracking determination unit 11 compares the calculated deviation amount with a predetermined threshold, thereby to determine whether or not normal tracking of the point X to look at by the target person is performed. Therefore, the spoofing detection unit is allowed to detect that the spoofing is performed on the basis of the determination result of the tracking determination unit 110. Specifically, when the calculated deviation amount is greater than the predetermined threshold, the tracking determination unit 110 determines that the normal tracking of the point X to look at by the target person is performed. In this case, the spoofing detection unit 201 detects that spoofing is performed. On the other hand, when the calculated deviation amount is less than the predetermined threshold, the tracking determination unit 110 determines that the normal tracking of the point X to look at by the target person is not performed. In this case, the spoofing detection unit 201 does not detect that the spoofing is performed. The spoofing detection unit 201 may be implemented as a functional block having the function described above, for example, in the CPU 11 (see FIG. 1).

The determination result output unit 202 is configured to output a determination result by the spoofing detection unit 201. The determination result output unit 202 may output only the result of whether or not the spoofing is performed, or may perform a predetermined operation (e.g., an alert operation) when it is detected that the spoofing is performed. The determination result output unit 202 may be implemented as a functional block having the function described above, for example, in the CPU 11 (see FIG. 1).

(Flow of Operation)

Next, with reference to FIG. 14, a flow of operation of the gaze estimation system 10 according to the fourth example embodiment will be described. FIG. 14 is a flowchart illustrating the flow of the operation of the gaze estimation system according to the fourth example embodiment.

Figure 14:
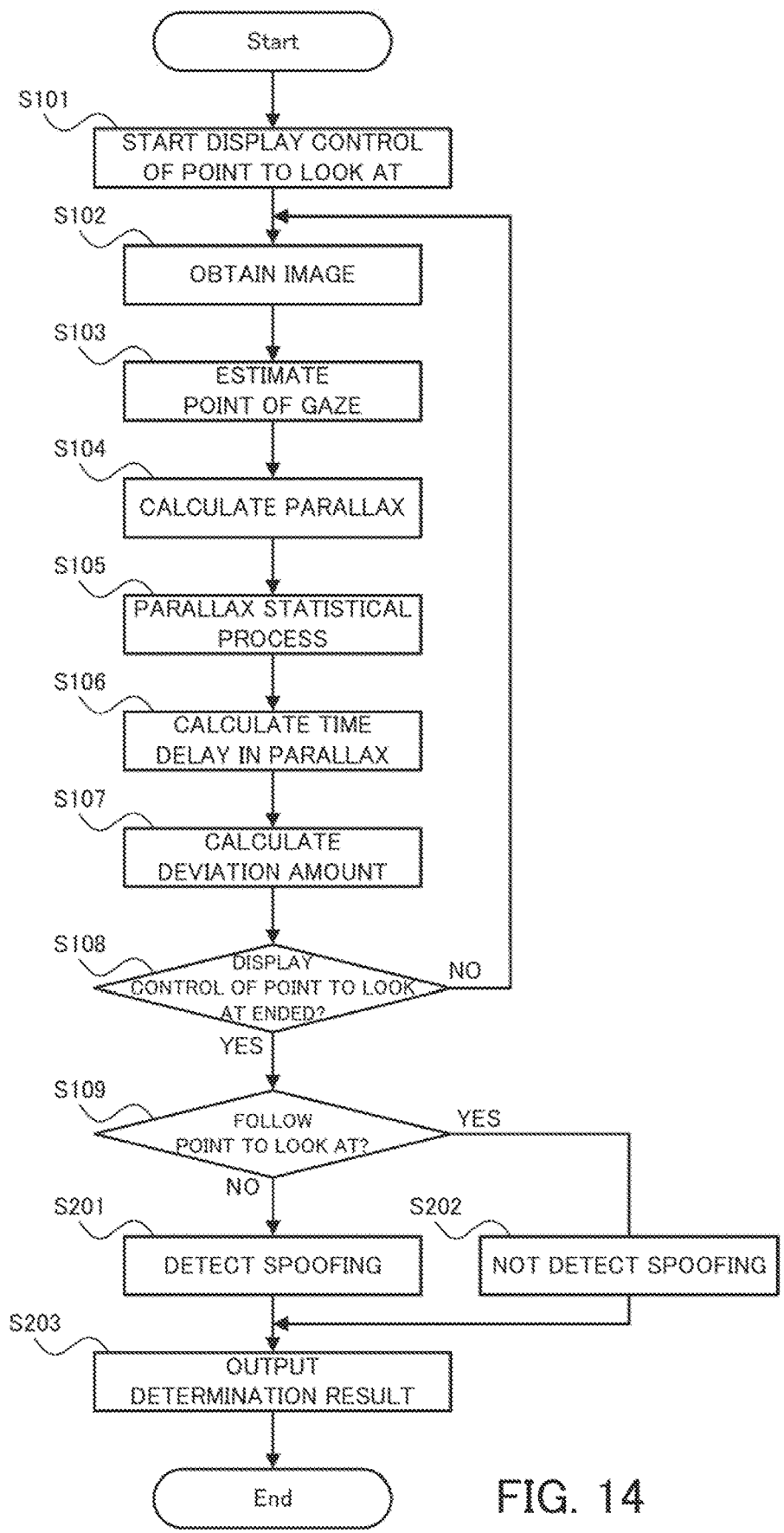
FIG. 14 is a flowchart illustrating a flow of operation of the gaze estimation system according to the fourth example embodiment.

As illustrated in FIG. 14, in operation of the gaze estimation system 10 according to the fourth example embodiment, as in the first example embodiment, first, the step S101 to the step S108 are performed. That is, the target person is asked to follow the point X to look at with the eyes, and the deviation between the estimated point of gaze and the true value is calculated from the image captured at that time.

Especially in the fourth example embodiment, when it is determined that the display control of the point to look at is ended (the step S108: YES), the tracking determination unit 110 determines whether or not the eyes of the target person have followed the point to look at (the step S109). When it is determined that the eyes of the target person have not followed the point to look at (the step S109: NO), the spoofing detection unit 201 detects that the spoofing is performed (step S201). On the other hand, when it is determined that the eyes of the target person have followed the point to look at (the step S109: YES), the spoofing detection unit 201 does not detect that the spoofing is performed (step S202). Then, the determination result output unit 202 outputs the determination result by the spoofing determination unit 201 (step S203).

In the fourth example embodiment, the spoofing may be detected by the spoofing detection unit 201 before the display control of the point X to look at is completed (in other words, the determination by the tracking determination unit 110 may be performed before the display control of the point X to look at is completed). For example, when determining that the calculated value of one deviation amount is a value corresponding to the spoofing, the tracking determination unit 110 determines that the tracking is not performed without waiting for the completion of the movement of the point X to look at, and at that timing, the spoofing detection unit 201 may detect that the spoofing is performed.

(Technical Effect)

Next, an example of a technical effect obtained by the gaze estimation system 10 according to the fourth example embodiment will be described.

As described in FIGS. 13 and 14, according to the gaze estimation system 10 in the fourth example embodiment, it is possible to determine and detect whether or not the spoofing is performed on the basis of the deviation amount calculated by the deviation amount calculation unit 106. That is, a difference between the movement of an actual point of gaze of a human and the movement of a mechanical point of gaze can be used to appropriately determine and detect the spoofing. The gaze estimation system 10 according to the fourth example embodiment exerts a beneficial effect, for example, when performing an authentication process using the point of gaze.

In the gaze estimation system 10 according to the fourth example embodiment, it is preferable not to display the trajectory of the point to look at. Alternatively, as illustrated in FIG. 10, it is preferable not to display the movement trajectory in which the point to look at will move from now, while displaying the movement trajectory in which the point to look at has already moved.

<Supplementary Notes>

The example embodiments described above may be further described as, but not limited to, the following Supplementary Notes.

(Supplementary Note 1)

A gaze estimation system described in Supplementary Note 1 is a gaze estimation system including: a display control unit that allows a point to look at where a target person looks at to be displayed to move in a predetermined moving aspect; a detection unit that detects a movement of eyes of the target person from an image of the target person; and a tracking determination unit that determines whether or not the eyes of the target person are following the point to look at on the basis of a relationship between the eye movement and a movement of the point to look at.

(Supplementary Note 2)

A gaze estimation system described in Supplementary Note 2 is the gaze estimation system described in Supplementary Note 1, wherein the display control unit allows the point to look at to be displayed in at least one of display aspects, which are: a first aspect in which the point to look at is moved so as to alternatively repeat a first period in which the point to look at is moved at a predetermined acceleration and a second period in which the point to look at is stopped for a predetermined period; a second aspect in which the point to look at is highlighted at regular intervals; a third aspect in which the point to look at is alternately displayed and not displayed at regular intervals; and a fourth aspect in which a size of the point to look at is changed during movement.

(Supplementary Note 3)

A gaze estimation system described in Supplementary Note 3 is the gaze estimation system described in Supplementary Note 1 or 2, wherein the display control unit allows a trajectory in which the point to look at passes and a trajectory in which the point to look at does not pass, from among movement trajectories of the point to look at, to be displayed in different display aspects, or allows at least one of the trajectory in which the point to look at passes and the trajectory in which the point to look at does not pass to be displayed.

(Supplementary Note 4)

A gaze estimation system described in Supplementary Note 4 is the gaze estimation system described in any one of Supplementary Notes 1 to 3, further including a correction unit that corrects a parameter related to the detected eye movement of the target person when the eyes of the target person are following the point to look at.

(Supplementary Note 5)

A gaze estimation system described in Supplementary Note 5 is the gaze estimation system described in Supplementary Note 4, wherein the correction unit calculates a parallax that is a difference between a position of the point to look at and a point of gaze of the target person, from the detected eye movement of the target person, calculates a time delay of the parallax from the parallax calculated in a state where the point to look at is moving, calculates a deviation amount of the estimated point of gaze with respect to a true value on the basis of the parallax and the time delay of the parallax, and determines a correction value for correcting the point of gaze of the target person on the basis of the deviation amount.

(Supplementary Note 6)

A gaze estimation system described in Supplementary Note 6 is the gaze estimation system described in Supplementary Note 5, wherein the correction unit calculates the deviation amount at a plurality of locations in an area in which the point to look at moves, and integrates a plurality of correction values determined on the basis of deviation amounts calculated at the plurality of locations, to thereby correct the point of gaze.

(Supplementary Note 7)

A gaze estimation system described in Supplementary Note 7 is the gaze estimation system described in any one of Supplementary Notes 1 to 6, further including a spoofing detection unit that detects spoofing of the target person when the eyes of the target person are not following the point to look at.

(Supplementary Note 8)

A gaze estimation system described in Supplementary Note 8 is the gaze estimation system described in Supplementary Note 7, wherein the spoofing detection unit calculates a parallax that is a difference between a position of the point to look at and a point of gaze of the target person, from the detected eye movement of the target person, calculates a time delay of the parallax from the parallax calculated in a state where the point to look at is moving, calculates a deviation amount of the estimated point of gaze with respect to a true value on the basis of the parallax and the time delay of the parallax, and determines the spoofing of the target person on the basis of the deviation amount.

(Supplementary Note 9)

A gaze estimation system described in Supplementary Note 9 is the gaze estimation system described in Supplementary Note 7 or 8, wherein the display control unit does not allow a movement trajectory of the point to look at to be displayed when the spoofing is detected by the spoofing detection unit.

(Supplementary Note 10)

A gaze estimation method described in Supplementary Note 10 is a gaze estimation method including: allowing a point to look at where a target person looks at to be displayed to move in a predetermined moving aspect; detecting a movement of eyes of the target person from an image of the target person; and determining whether or not the eyes of the target person are following the point to look at on the basis of a relationship between the eye movement and a movement of the point to look at.

(Supplementary Note 11)

A computer program described in Supplementary Note 11 is a computer program that operates a computer: to allow a point to look at where a target person looks at to be displayed to move in a predetermined moving aspect; to detect a movement of eyes of the target person from an image of the target person; and to determine whether or not the eyes of the target person are following the point to look at on the basis of a relationship between the eye movement and a movement of the point to look at.

This disclosure is not limited to the examples described above and is allowed to be changed, if desired, without departing from the essence or spirit of the invention which can be read from the claims and the entire specification. A gaze estimation system, a gaze estimation method, and a computer program with such modifications are also intended to be within the technical scope of this disclosure

DESCRIPTION OF REFERENCE CODES

10 Gaze estimation system
20 Display unit
30 Imaging unit
101 Display control unit
102 Movement detection unit
103 Parallax calculation unit
104 Statistical processing unit
105 Time delay calculation unit
106 Deviation amount calculation unit
107 Correction value integration unit
108 Gaze point correction output unit
110 Tracking determination unit
201 Spoofing detection unit
202 Determination result output unit

What is claimed is:

1. A gaze estimation system comprising:
at least one memory storing instructions; and
at least one processor that is configured to execute instructions to:
allow a point to look at where a target person looks at to be displayed to move in a predetermined moving aspect;
detect a movement of eyes of the target person from an image of the target person;
determine whether or not the eyes of the target person are following the point to look at on the basis of a relationship between the eye movement and a movement of the point to look at;
calculate a parallax that is a difference between a position of the point to look at and a point of gaze of the target person, from the detected eye movement of the target person,
calculate a time delay of the parallax from the parallax calculated in a state where the point to look at is moving,
calculate a deviation amount of the estimated point of gaze with respect to a true value on the basis of the parallax and the time delay of the parallax, and
determine a correction value for correcting the point of gaze of the target person on the basis of the deviation amount; and
correct a parameter related to the detected eye movement of the target person when the eyes of the target person are following the point to look at.

2. The gaze estimation system according to claim 1, wherein the processor allows the point to look at to be displayed in at least one of display aspects, which are: a first aspect in which the point to look at is moved so as to alternatively repeat a first period in which the point to look at is moved at a predetermined acceleration and a second period in which the point to look at is stopped for a predetermined period; a second aspect in which the point to look at is highlighted at regular intervals; a third aspect in which the point to look at is alternately displayed and not displayed at regular intervals; and a fourth aspect in which a size of the point to look at is changed during movement.

3. The gaze estimation system according to claim 1, wherein the at least one processor allows a trajectory in which the point to look at passes and a trajectory in which the point to look at does not pass, from among movement trajectories of the point to look at, to be displayed in different display aspects, or allows at least one of the trajectory in which the point to look at passes and the trajectory in which the point to look at does not pass to be displayed.

4. The gaze estimation system according to claim 1, wherein
the at least one processor
calculates the deviation amount at a plurality of locations in an area in which the point to look at moves, and
integrates a plurality of correction values determined on the basis of deviation amounts calculated at the plurality of locations, to thereby correct the point of gaze.

5. The gaze estimation system according to claim 1, wherein the at least one processor is configured to execute the instructions to detect spoofing of the target person when the eyes of the target person are not following the point to look at.

6. The gaze estimation system according to claim 5, wherein
the at least one processor
determines the spoofing of the target person on the basis of the deviation amount.

7. A gaze estimation method performed by a computer and comprising:
allowing a point to look at where a target person looks at to be displayed to move in a predetermined moving aspect;
detecting a movement of eyes of the target person from an image of the target person;
determining whether or not the eyes of the target person are following the point to look at on the basis of a relationship between the eye movement and a movement of the point to look at;

calculating a parallax that is a difference between a position of the point to look at and a point of gaze of the target person, from the detected eye movement of the target person, calculating a time delay of the parallax from the parallax calculated in a state where the point to look at is moving, calculating a deviation amount of the estimated point of gaze with respect to a true value on the basis of the parallax and the time delay of the parallax, and determining a correction value for correcting the point of gaze of the target person on the basis of the deviation amount; and correcting a parameter related to the detected eye movement of the target person when the eyes of the target person are following the point to look at.

8. A non-transitory recording medium storing a computer program executable by a computer to perform a gaze estimation method comprising:

allowing a point to look at where a target person looks at to be displayed to move in a predetermined moving aspect;

detecting a movement of eyes of the target person from an image of the target person;

determining whether or not the eyes of the target person are following the point to look at on the basis of a relationship between the eye movement and a movement of the point to look at;

calculating a parallax that is a difference between a position of the point to look at and a point of gaze of the target person, from the detected eye movement of the target person, calculating a time delay of the parallax from the parallax calculated in a state where the point to look at is moving, calculating a deviation amount of the estimated point of gaze with respect to a true value on the basis of the parallax and the time delay of the parallax, and determining a correction value for correcting the point of gaze of the target person on the basis of the deviation amount; and correcting a parameter related to the detected eye movement of the target person when the eyes of the target person are following the point to look at.

* * * * *